US010785610B2

(12) United States Patent
Bohlander et al.

(10) Patent No.: US 10,785,610 B2
(45) Date of Patent: *Sep. 22, 2020

(54) EVENT-BASED RESPONDER DISPATCH

(71) Applicant: Axon Enterprise, Inc., Scottsdale, AZ (US)

(72) Inventors: Michael J. Bohlander, Seattle, WA (US); Raymond T. Fortna, Seattle, WA (US); Anthony G. Huang, Seattle, WA (US); Jeffrey P. Jolma, Seattle, WA (US); Julianne C. Weiss, Los Angeles, CA (US); Aerianna K. Deluca, Seattle, WA (US)

(73) Assignee: Axon Enterprise, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/367,034

(22) Filed: Mar. 27, 2019

(65) Prior Publication Data

US 2019/0222972 A1 Jul. 18, 2019

Related U.S. Application Data

(63) Continuation of application No. 15/993,247, filed on May 30, 2018, now Pat. No. 10,264,412, which is a
(Continued)

(51) Int. Cl.
*H04W 4/08* (2009.01)
*H04W 4/02* (2018.01)
(Continued)

(52) U.S. Cl.
CPC ............. *H04W 4/08* (2013.01); *A61B 5/0004* (2013.01); *A61B 5/0008* (2013.01);
(Continued)

(58) Field of Classification Search
None
See application file for complete search history.

(56) References Cited

U.S. PATENT DOCUMENTS

| 6,621,422 B2 | 9/2003 | Rubenstein |
| 7,034,678 B2 | 4/2006 | Burkley |

(Continued)

FOREIGN PATENT DOCUMENTS

| CN | 203468597 U | 3/2014 |
| WO | 2006047597 | 5/2006 |
| WO | 2008027750 | 3/2008 |

*Primary Examiner* — Fayyaz Alam
(74) *Attorney, Agent, or Firm* — Andrew Graham

(57) ABSTRACT

Dispatch-aiding communications between computing devices of a responder and a dispatch unit include a computing device of the responder determining that an event occurred, automatically sending an indication of the event to a computing device of the dispatch unit, receiving a request for information from the computing device of the dispatch unit, obtaining the information requested by the computing device of the dispatch unit, and sending the information requested by the computing device of the dispatch unit to the computing device of the dispatch unit. The computing device of the dispatch unit sends the request for information to the computing device of the responder in response to receiving the indication of the event.

26 Claims, 10 Drawing Sheets

Related U.S. Application Data continuation of application No. 15/462,820, filed on Mar. 18, 2017, now Pat. No. 10,002,520, which is a continuation of application No. 14/860,352, filed on Sep. 21, 2015, now Pat. No. 9,642,131, application No. 16/367,034.

(51) Int. Cl.

| | |
|---|---|
| *H04W 68/00* | (2009.01) |
| *H04N 5/77* | (2006.01) |
| *A61B 5/00* | (2006.01) |
| *A61B 5/024* | (2006.01) |
| *H04W 4/029* | (2018.01) |
| *A61B 5/0205* | (2006.01) |
| *G16H 40/67* | (2018.01) |
| *H04N 21/81* | (2011.01) |
| *H04W 4/90* | (2018.01) |
| *A61B 5/021* | (2006.01) |
| *A61B 5/026* | (2006.01) |
| *A61B 5/08* | (2006.01) |
| *A61B 5/1455* | (2006.01) |
| *H04M 3/51* | (2006.01) |
| *H04N 7/18* | (2006.01) |
| *H04W 4/30* | (2018.01) |
| *G08B 25/00* | (2006.01) |
| *H04L 29/06* | (2006.01) |
| *H04W 4/35* | (2018.01) |
| *H04N 9/82* | (2006.01) |

(52) U.S. Cl.
CPC ............ *A61B 5/0022* (2013.01); *A61B 5/021* (2013.01); *A61B 5/024* (2013.01); *A61B 5/0205* (2013.01); *A61B 5/026* (2013.01); *A61B 5/02438* (2013.01); *A61B 5/08* (2013.01); *A61B 5/14551* (2013.01); *A61B 5/747* (2013.01); *G08B 25/006* (2013.01); *G08B 25/007* (2013.01); *G16H 40/67* (2018.01); *H04L 65/4084* (2013.01); *H04M 3/5116* (2013.01); *H04N 5/77* (2013.01); *H04N 7/188* (2013.01); *H04N 21/814* (2013.01); *H04W 4/02* (2013.01); *H04W 4/023* (2013.01); *H04W 4/025* (2013.01); *H04W 4/029* (2018.02); *H04W 4/30* (2018.02); *H04W 4/90* (2018.02); *H04W 68/005* (2013.01); *H04M 2242/04* (2013.01); *H04M 2250/12* (2013.01); *H04N 9/8205* (2013.01); *H04W 4/35* (2018.02)

(56) References Cited

U.S. PATENT DOCUMENTS

| | | |
|---|---|---|
| 7,091,851 B2 | 8/2006 | Mason |
| 7,091,852 B2 | 8/2006 | Mason |
| 7,177,623 B2 | 2/2007 | Baldwin |
| 7,245,216 B2 | 7/2007 | Burkley |
| 7,337,068 B2 | 2/2008 | Valero et al. |
| 7,502,687 B2 | 3/2009 | Flick |
| 7,508,840 B2 | 3/2009 | Delaney |
| 7,652,571 B2 | 1/2010 | Parkulo |
| 7,925,246 B2 | 4/2011 | McKibben |
| 7,937,068 B2 | 5/2011 | Hogberg et al. |
| 8,013,734 B2 | 9/2011 | Saigh |
| 8,026,791 B2 | 9/2011 | Kreiner |
| 8,260,338 B2 | 9/2012 | Shaffer |
| 8,275,404 B2 | 9/2012 | Berger |
| 8,314,683 B2 | 11/2012 | Pfeffer |
| 8,504,090 B2 | 8/2013 | Klein |
| 8,520,700 B2 | 8/2013 | Greene |
| 8,526,934 B2 | 9/2013 | Sennett |
| 8,600,338 B2 | 12/2013 | Perrott |
| 8,665,087 B2 | 3/2014 | Greene |
| 8,688,375 B2 | 4/2014 | Funk |
| 8,866,606 B1 | 10/2014 | Will |
| 8,873,719 B2 | 10/2014 | Clawson |
| 9,125,041 B2 | 9/2015 | Greene |
| 9,191,992 B2 * | 11/2015 | Dimitri ................. H04W 88/06 |
| 2003/0028536 A1 | 2/2003 | Singh |
| 2004/0095954 A1 | 5/2004 | Varney et al. |
| 2007/0103292 A1 | 5/2007 | Burkley |
| 2007/0250348 A1 | 10/2007 | D'Ambrosia |
| 2008/0001735 A1 | 1/2008 | Tran |
| 2008/0037461 A1 | 2/2008 | Biltz |
| 2008/0057992 A1 | 3/2008 | Griffin |
| 2008/0181132 A1 | 7/2008 | Underhill |
| 2011/0018992 A1 | 1/2011 | Guzik |
| 2011/0071880 A1 | 3/2011 | Spector |
| 2011/0197202 A1 | 8/2011 | Lodolo |
| 2011/0197272 A1 | 8/2011 | Lodolo |
| 2013/0005294 A1 * | 1/2013 | Levinson ................. H04N 7/18 455/404.2 |
| 2013/0082837 A1 | 4/2013 | Cosentino |
| 2013/0342361 A1 | 12/2013 | Greene |
| 2014/0187280 A1 | 7/2014 | Bekiares et al. |
| 2014/0243036 A1 | 8/2014 | Kouwe |
| 2014/0266690 A1 | 9/2014 | McKinley |
| 2014/0368601 A1 * | 12/2014 | deCharms ............ H04W 4/021 348/14.02 |
| 2015/0094013 A1 * | 4/2015 | Dimitri ................. H04W 88/06 455/404.2 |
| 2015/0256990 A1 * | 9/2015 | Vilrokx ................. H04W 76/50 455/404.1 |
| 2015/0347079 A1 | 12/2015 | Price |
| 2016/0105773 A1 * | 4/2016 | Wawrowski .......... H04W 4/029 455/456.2 |
| 2016/0135029 A1 * | 5/2016 | Johnson ................. H04W 76/10 455/404.2 |

* cited by examiner

EVENT-BASED RESPONDER DISPATCH

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one embodiment, a method of communicating between a responder and a dispatch unit includes a computing device of the responder determining that an event occurred where the event is associated with the responder, automatically sending an indication of the event to a computing device of the dispatch unit in response to determining that the event occurred, receiving a request for information from the computing device of the dispatch unit, obtaining the information requested by the computing device of the dispatch unit, and sending the information requested by the computing device of the dispatch unit to the computing device of the dispatch unit. The computing device of the dispatch unit is configured to send the request for information to the computing device of the responder in response to receiving the indication of the event.

In one example, the information requested by the computing device of the dispatch unit includes live video and sending the information requested by the computing device of the dispatch unit includes streaming the live video from the computing device of the responder to the computing device of the dispatch unit. In another example, obtaining the information requested by the computing device of the dispatch unit includes the computing device of the responder enabling a camera associated with the responder and receiving the live video from the enabled camera.

In another example, the method further includes the computing device of the responder adding metadata to the information requested by the computing device of the dispatch unit prior to sending the information requested by the computing device of the dispatch unit. In another example, the metadata includes one or more of a dispatch record number, an identifier of a responder agency, a location, or a category of the requested information.

In another example, the method further includes the computing device of the responder receiving a request to enable or disable at least one device associated with the responder, determining that the request to enable or disable at least one device was sent by an authorized sender, and enabling or disabling the at least one device. In another example, the at least one device includes at least one of a camera, a microphone, a weapon, a light bar, or a safety device.

In another example, the event includes one or more of a heart rate of the responder exceeds a threshold, a safety device is disabled, a gunshot sound is detected, the responder is determined to be nonresponsive, the responder presses a panic button, the officer enters information into the computing device of the responder, or the computing device of the responder arrives at a particular location or event.

In another embodiment, a non-transitory computer readable medium has instructions embodied thereon for managing a plurality of responders, where each of the plurality of responders has a computing device. The instructions, in response to execution by a dispatch computing device, cause the dispatch computing device to determine that the computing devices of the plurality of responders are located in proximity to a location or event, determine a hierarchy of the plurality of responders, send an indication of the hierarchy to each of the computing devices of the plurality of responders, and establish a communication link between the computing devices of the plurality of responders. The computing devices of the plurality of responders are configured to communicate with each other via the communication link based on the hierarchy received from the dispatch computing device.

In one example, the plurality of responders includes responders from different responder agencies or different organizations of a responder agency.

In another example, the instructions, in response to execution by the dispatch computing device, further cause the dispatch computing device to receive an indication of a subset of the plurality of responders and send information to one or more computing devices associated with the plurality of responders in the subset.

In another example, the instructions, in response to execution by the dispatch computing device, further cause the dispatch computing device to receive, from the computing devices of the plurality of responders, biometric data about the plurality of responders. In another example, the biometric data includes indications of stress levels of the plurality of responders.

In another example, the instructions, in response to execution by the dispatch computing device, further cause the dispatch computing device to dispatch one or more of the plurality of responders to a location, where the indications of stress levels of the plurality of responders indicate that a stress level of each of the one or more of the plurality of responders is below a threshold stress level. In another example, the instructions, in response to execution by the dispatch computing device, further cause the dispatch computing device to determine, based on the indications of stress levels of the plurality of responders, that a stress level of a first responder of the plurality of responders is above a threshold and to dispatch a second responder of the plurality of responders to a location of the first responder in response to determining that the stress level of the first responder is above the threshold.

In another example, the instructions, in response to execution by the dispatch computing device, further cause the dispatch computing device to receive responder status information from the computing devices of the plurality of responders and to display an indication of the responder status information for at least one responder of the plurality of responders. In another example, the displayed indication of the responder status includes an indication of one or more of whether the at least one responder is inside or outside of a vehicle, whether hardware of the at least one responder is activated, whether a light bar of the at least one responder is active, or whether a stress level of the at least one responder exceeds a threshold.

In another example, the instructions, in response to execution by the dispatch computing device, further cause the dispatch computing device to receive, from one of the computing devices of the plurality of responders, a request to activate cameras within a geographic range and to activate the cameras within the geographic range in response to receiving the request to activate the cameras. In another example, the instructions, in response to execution by the dispatch computing device, further cause the dispatch computing device to send an alert to one or more of a supervisor of a responder associated with the one of the computing devices or at least one of the plurality of responders in response to receiving the request to activate the cameras.

In another embodiment, a computing device for communicating between a responder and a dispatch unit includes a processor and a computer readable medium having instructions embodied thereon. The instructions, in response to execution by the processor, cause the computing device to determine that an event occurred where the event is associated with the responder, automatically send an indication of the event to a dispatch computing device in response to determining that the event occurred, receive a request for information from the computing device of the dispatch computing device, obtain the information requested by the computing device of the dispatch unit, and send the information requested by the dispatch computing device to the dispatch computing device. The dispatch computing device is configured to send the request for information to the computing device in response to receiving the indication of the event,

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
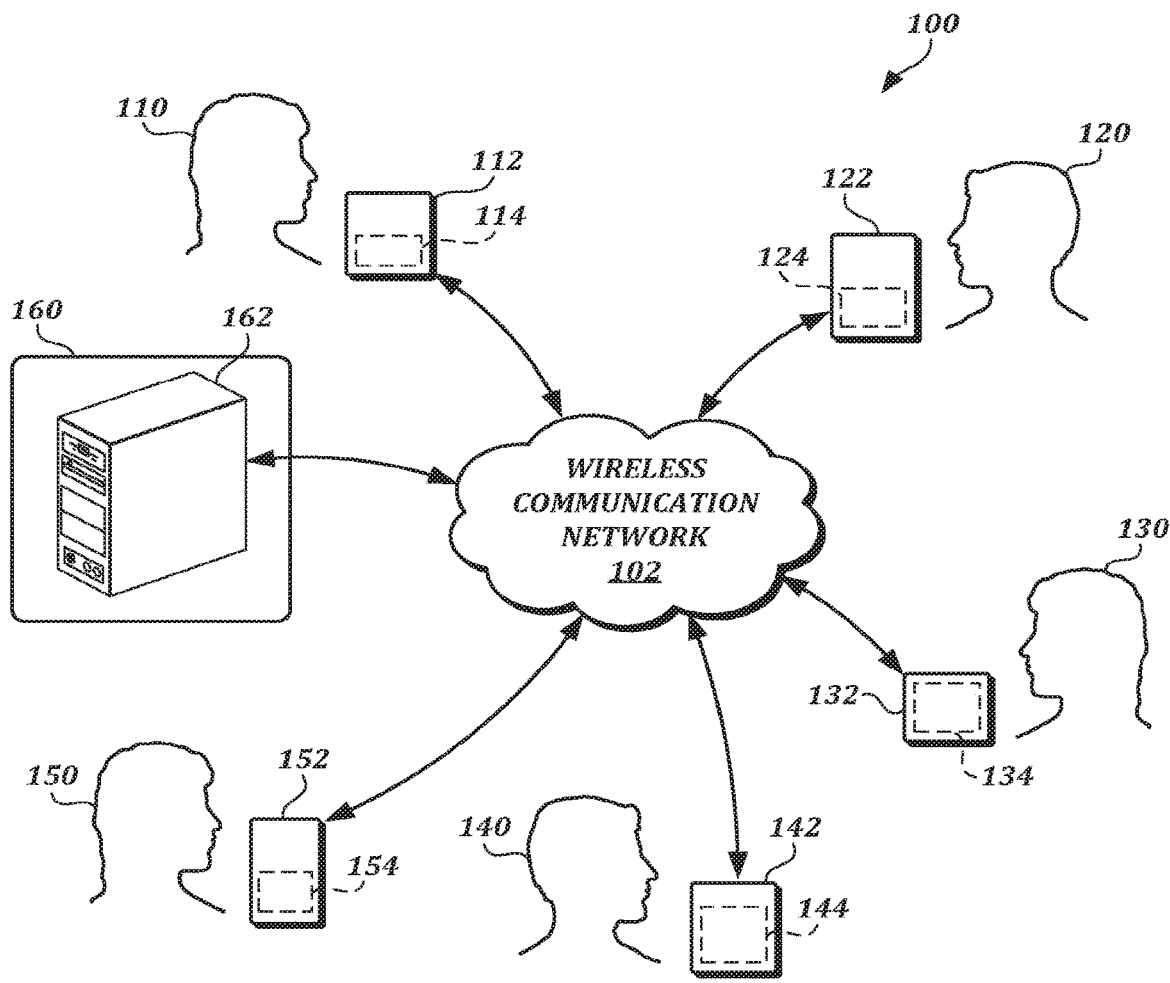
FIG. 1 depicts an embodiment of a system for communication between computing devices of responders via a network, in accordance with the embodiments disclosed herein.

Embodiments of the present disclosure are generally directed to techniques and tools for communicating between a computing device of a responder and a computing device of a dispatch unit. Legacy communication systems allow responders to communicate. For example, many law enforcement departments use radios to communicate live audio between law enforcement officers (e.g., officers on duty, their supervisors, dispatchers, etc.). However, legacy communication systems have many downfalls. For example, legacy communication systems are manually activated, such as in the case pressing a button during audio transmissions. Manual activation of communication systems takes responders' time and attention away from other matters. For example, if a police officer sends a radio communication while driving to pursue a suspect, some time and attention will be diverted away from driving to activate the communication system and send a transmission. In another example, a police officer may draw a weapon to deter a threat and not be able to activate the communication system without diverting attention away from deterring the threat. In this last example, deterring the threat with the weapon may prevent the police officer from sending a communication requesting backup even though requesting backup may be an urgent need of the police officer. In another example, legacy communication systems (e.g., radio communication systems) typically allow for only one user to transmit information at one time. If two responders send competing transmissions, generally the two transmissions cancel each other out and neither transmission is heard.

In various embodiments disclosed herein, systems and methods of communication by and between computing devices of responders and dispatch units are discussed. A responder is any individual that is part of an agency that responds to particular situations. Examples of responders include law enforcement officials, firefighting officials, paramedics, private security personnel, private responders (e.g., tow truck drivers and roadside assistance personnel), and the like. Law enforcement officials include police officers, sheriffs and sheriff deputies, state patrol officers, federal agency officers (e.g., Federal Bureau of Investigation agents, Central Intelligence Agency agents, Transportation Security Administration officers, etc.), members of the National Guard, members of the armed forces, and the like. Examples of responders also include supervisors (e.g., police sergeants) and dispatchers of other responders. Examples of responder agencies include police departments, sheriff offices, fire departments, federal agencies, private companies of private security personnel, private responders, and the like.

A dispatch unit coordinates actions of responders. In one example, a dispatch unit includes computing devices usable to dispatch responders, such as to dispatch responders to particular events. Examples of dispatch units include police dispatch units that dispatch police officers, fire dispatch units that fire fighters and and/or paramedics, private security offices that dispatch private security personnel, and the like.

In one or more embodiments disclosed herein, a computing device of a responder determines that an event occurred and automatically sends an indication of the event to a computing device of a dispatch unit. The computing device of the dispatch unit sends the request for information to the computing device of the responder in response to receiving the indication of the events and the computing device of the responder obtains the requested information and sends it back to the computing device of the dispatch unit. When certain events occur, these example embodiments allow a dispatch unit to be alerted to the event and to gain more information about the event without the responder interacting with the computing device or any other communication system.

In one or more other embodiments disclosed herein, a dispatch computing device determines that computing devices of responders are located in proximity to a location or event, determines a hierarchy of the plurality of responders, and sends an indication of the hierarchy to computing devices of the responders. The dispatch computing device also establishes a communication link between the computing devices of the responders and the computing devices of the responders are configured to communicate with each other via the communication link based on the hierarchy received from the dispatch computing device. This allows responders to communicate with other responders in a hierarchy even when the responder is not aware of the hierarchy. For example, a determined hierarchy may include responders from multiple agencies who are in proximity to a location or event. Even if the responder does not know the hierarchy, the responder can send communications based on the hierarchy (e.g., to other responders under the responder in the hierarchy, to other responders at the same level as the responder in the hierarchy, to other responders above the responder in the hierarchy, etc.). In addition, this also allows responders to communicate with responders from other responder agencies in the hierarchy when traditional communication systems (e.g., voice radios) are not configured to allow inter-agency communications.

In the following description, numerous specific details are set forth in order to provide a thorough understanding of illustrative embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein. The illustrative examples provided herein are not intended to be exhaustive or to limit the claimed subject matter to the precise forms disclosed.

FIG. 1 depicts an embodiment of a system 100 for communication between computing devices of responders via a network 102. The system includes a responder 110 that has a computing device 112 that is capable of communicating via the network 102. In some embodiments, the network 102 is a wireless communication network using one or more wireless communication protocols, such as WiFi, 2G, 3G, 4G, LTE, WiMAX, Bluetooth, and the like. In the depicted embodiment, the computing device 112 includes a communication application 114 that includes instructions that cause the computing device 112 to establish a communication link between computing devices of other responders via the network 102.

The system 100 also includes responders 120, 130, 140, and 150. Each of the responders 120, 130, 140, and 150 has one of computing devices 122, 132, 142, and 152 that is capable of communicating via the network 102. Each of the computing devices 122, 132, 142, and 152 includes one of the communication applications 124, 134, 144, 154 that includes instructions that cause the computing devices 122, 132, 142, and 152 to establish a communication link between computing devices of other responders via the network 102.

In the depicted embodiment, the system 100 also includes a dispatch unit 160 that includes a computing device 162. In some examples, the computing device 162 includes one or more of a server, a desktop computer, a laptop computer, a tablet computer, and the like. The computing device 162 is capable of communicating via the network 102. The computing device 162 includes a communication application that includes instructions that cause the computing device 162 to establish a communication link between computing devices of other responders via the network 102. In one embodiment, the computing device 162 is used by a responder, such as a dispatcher, a supervisory responder, or any other type of responder.

In some embodiments, each of the computing devices 112, 122, 132, 142, 152, and 162 includes one or more of a cell phone, tablet computer, smart wearable (e.g., a smart watch), a laptop computer, a desktop computer, and the like. In one example, the computing devices 112, 122, 132, 142, and 152 are personal devices of the responders 110, 120, 130, 140, and 150 and are not issued by any responder agency of the responders 110, 120, 130, 140, and 150. In that case, the communication applications 114, 124, 134, 144, and 154 are configured to enable communication between the personal computing devices 112, 122, 132, 142, and 152 of the responders 110, 120, 130, 140, and 150 with each other and with computing devices of one or more responder agencies, such as computing device 162.

In another example, when communicating via the network 102, the computing devices 112, 122, 132, 142, 152, and 162 are capable of sending communications directly to another of the computing devices 112, 122, 132, 142, 152, and 162 (i.e., direct communication), to a subset of the computing devices 112, 122, 132, 142, 152, and 162 (i.e., selective communication), or to all of the computing devices 112, 122, 132, 142, 152, and 162 (i.e., broadcast communication). In some embodiments, as discussed in greater detail below, communications are sent between one or more of the computing devices 112, 122, 132, 142, 152, and 162 via a communication link based on a priority rank among at least two of the responders 110, 120, 130, 140, and 150.

In some embodiments, the responders 110, 120, 130, 140, and 150 are all associated with the same responder agency. Examples of responders from the same responder agency include police officers from the same police department, firefighters from the same fire department, private security personnel from the same organization, and the like. In other embodiments, at least some of the responders 110, 120, 130, 140, and 150 are associated with different responder agencies. Examples of responders from different responder agencies include police officers from one police department and police officers from another police department, state patrol officers and sheriffs deputies, federal agency agents and members of the armed forces, and the like.

Figure 2:
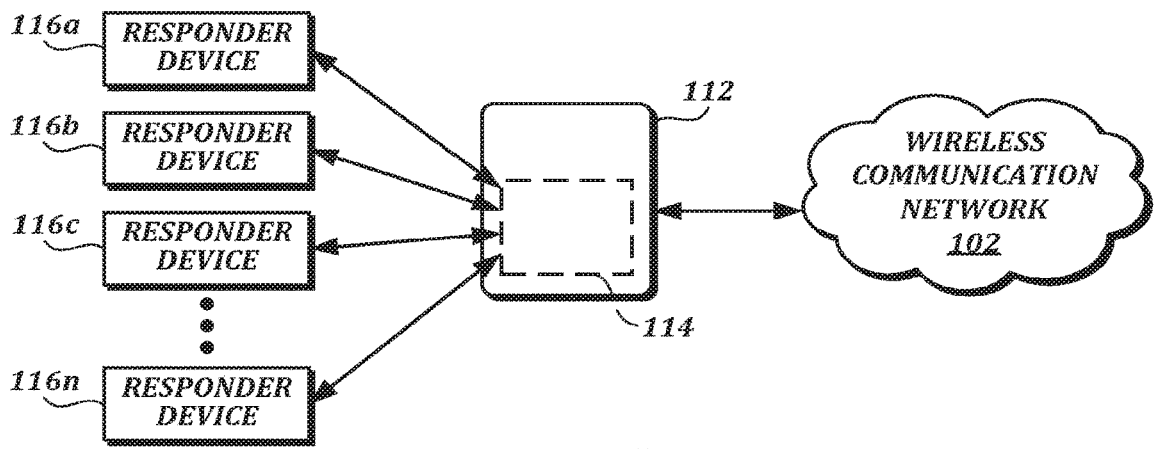
FIG. 2 depicts an embodiment of capabilities of a computing device depicted in FIG. 1, in accordance with embodiments of computing devices disclosed herein.

An embodiment of the capabilities of the computing device 112 is depicted in FIG. 2. As described above, the computing device 112 includes the communications application 114 and is capable of communicating via the network 102. The computing device 112 is also capable of communicating with any number of responder devices 116a-n. Examples of the responder devices 116a-n include devices worn or carried by the responder 110, such as an on-body camera, a conducted electrical weapon (CEW), a firearm holster, an on-body microphone, a radio, and the like. Other examples of the responder devices 116a-n include devices associated with a vehicle of the responder 110, such as a light bar, a dashboard camera, a microphone, an in-vehicle sensor, and the like. The responder devices 116a-n can include any other device associated with the responder 110.

In some embodiments, the communications application 114 includes instructions that, when executed, cause the computing device 112 to send communications via the network 102 to computing devices of other responders. In some embodiments, the communications include information provided by at least one of the responder devices 116a-n. In some examples, the communication can include video from an on body camera, audio from an on-body microphone, and the like. In some embodiments, the communication can include information indicative of a status change of the responder devices 116a-n. In some examples, the communication includes an indication that a light bar of a vehicle has been activated, an indication that a holster has been unlocked to allow removal of a firearm, and the like. In other examples, the responder devices 116a-n include one or more biometric sensors configured to generate biometric data about the responder 110, such as a heart rate, body temperature, blood pressure, and the like. In other embodiments, the communication can include information from the computing device 112. In some examples, the communication includes audio captured by a microphone of the computing device 112, text entered into the computing device 112, and the like.

In another embodiment, the communications application 114 includes instructions that, when executed, cause the computing device 112 to process information prior to sending it via the network 102. In one example, the communications application 114 causes the computing device 112 to reduce a resolution of the information (e.g., pictures, recorded video, video streams, etc.) prior to sending the information via the network 102. In another example, the communications application 114 causes the computing device 112 to tag the information with metadata (e.g., a time of capture of the information, a location of capture of the information, etc.) prior to sending the information via the network 102. In another example, the communications application 114 causes the computing device 112 to compile multiple forms of information (e.g., text and images) into a single transmission via the network 102.

The depiction in FIG. 2 includes an embodiment of the computing device 112. However, this embodiment is not limited only to computing device 112. Any of the other computing devices described herein, such as computing devices 122, 132, 142, 152, and 162, may have similar capabilities to communicate via the network 102 and to communicate with responder devices associated with the computing devices.

Figure 3:
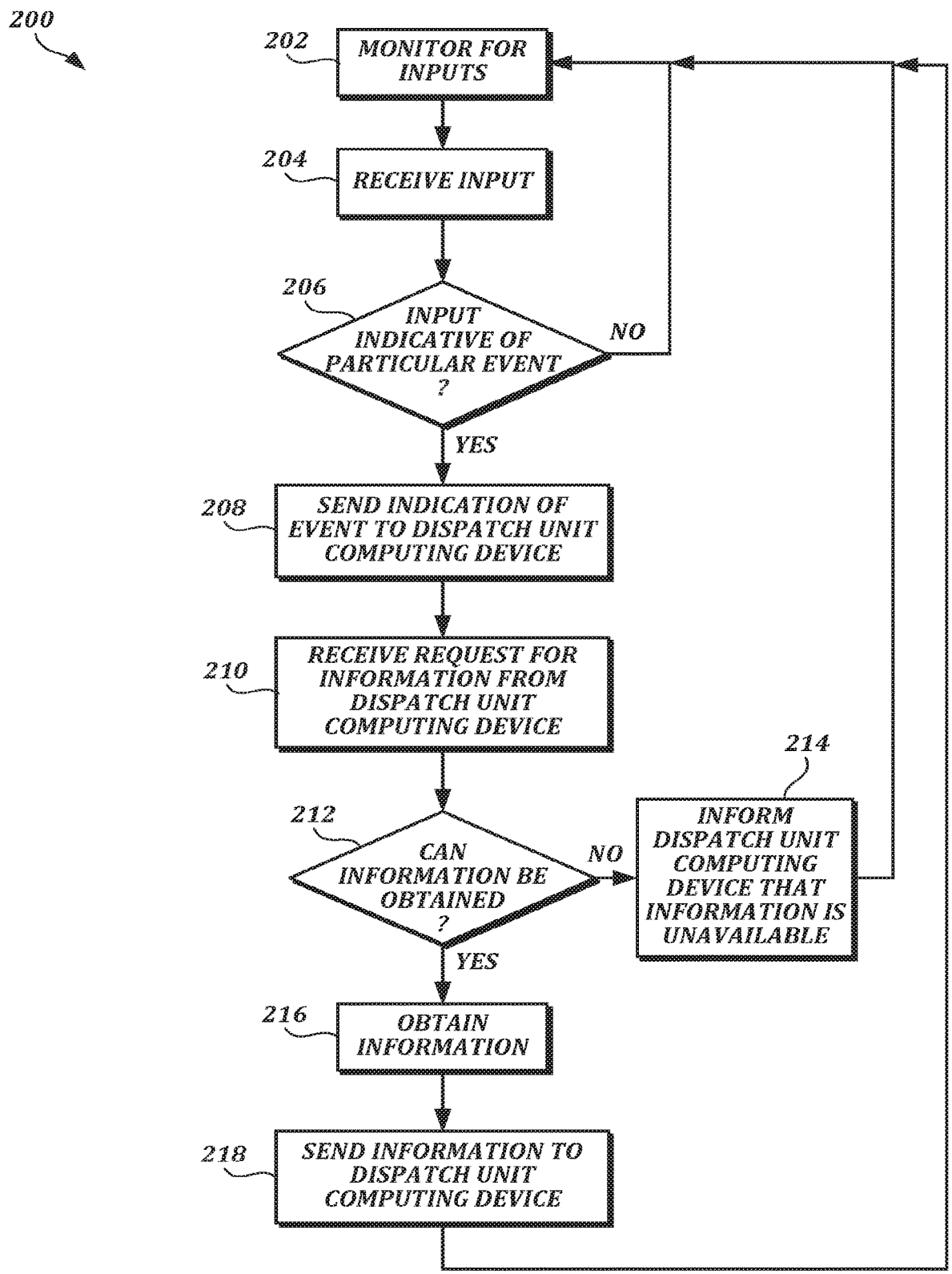
FIG. 3 depicts an embodiment of a method for a computing device of a responder to facilitate communication between a responder and a dispatch unit, in accordance with embodiments of computing devices disclosed herein.

An embodiment of a method 200 for a computing device of a responder to facilitate communication between a responder and a dispatch unit is depicted in FIG. 3. At block 202, the computing device (e.g., one of computing devices 122, 132, 142, 152) monitors for inputs. In some examples, the computing device monitors for inputs from responder devices (e.g., responder devices 116a-n), such as inputs indicating biometric data about the responder, statuses of the responder devices (e.g., holster open or closed, light bar on or off, etc.), and the like. In another example, the computing device monitors for inputs directly from one or more components of the computing device, such as sound via a microphone of the computing device, an image or images via a camera of the computing device, a user input via an input mechanism of the computing device, and the like. In another embodiment, the computing device monitors for a signal from another device (e.g., a gunshot sound monitor) that is in communication with the computing device. At block 204, the computing device receives an input. In some examples, the computing device receives an input from one of the responder devices or the computing device receives an input directly from one or more components of the computing device.

At block 206, the computing device decides whether the input is indicative of a particular event. In some examples, inputs may be binary, such as indications that a holster is open or closed, indications that a light bar is on or off, and the like. In other examples, inputs may not be binary and the computing device processes the input to determine whether the input is indicative of a particular event. In one example, the computing device receives sound via a microphone and processes the received sound to determine whether the received sound is indicative of a particular event (e.g., a gunshot). In another example, the computing device receives biometric data about the responder from one or more biometric sensors and processes the biometric data to determine whether a stress level of the responder exceeds a stress threshold. If, at block 206, the computing device determines that the input is not indicative of a particular event, then the method returns back to block 202 to monitor for additional inputs. However, if, at block 206, the computing device determines that the input is indicative of a particular event, then the method proceeds to block 208.

At block 208, the computing device sends an indication of the particular event to a dispatch unit computing device. In one embodiment, the computing device is configured to automatically send the indication of the particular event to the dispatch unit computing device in response to determining that the input is indicative of the particular event. Automatically sending the indication permits the dispatch unit computing device to be informed of the event without the responder or any other user interacting with the computing device. Automatic sending may be beneficial in circumstances when the responder's attention is or should be focused elsewhere, such as when the responder activates a light bar, when the responder opens a holster to remove a weapon, and the like. In one embodiment, the computing device sends the indication to the dispatch unit computing device via a network, such as a cellular network, a WiFi network, a local area network, any other network, or any combination thereof.

At block 210, the computing device receives a request for information from the dispatch computing device. In some embodiments, the request for information includes a request for data from the computing device or a responder device in communication with the computing device. In one example, the request for information includes a request for a live video stream from a camera, such as a camera positioned on the body of the responder, a camera positioned on a dashboard of the responder's vehicle, or any other camera. In another example, the request for information includes a request for a live audio stream, such as a live audio stream of sound received by a microphone of the computing device. In another example, the request for information includes a request for other information, such as a location of the computing device, a speed of the computing device or the responder's vehicle, a stress level of the responder, biometric data about the responder, or any other kind of information.

At block 212, the computing device determines whether the requested information can be obtained. In some embodiments, the computing device may not be able to obtain the information. For example, if the requested information is for biometric data about the responder and there are no biometric sensors in communication with the computing device, the computing device cannot obtain the requested information. In some embodiments, the computing device may have immediate access to the requested information. For example, the requested information may be for a live audio stream and the computing device may already have access to live audio signals generated by a microphone of the computing device. In other embodiments, the computing device is able to obtain the information by enabling a responder device. In one example, the responder wears a body camera that begins streaming video when enabled and the computing device enables the body camera to begin streaming video. If, at block 212, the computing device determines that the requested information is not available, then, at block 214, the computing device informs the dispatch unit computing device that the requested information is not available and the method returns back to block 202 to monitor for additional inputs. However, if, at block 212, the computing device determines that the requested information can be obtained, then the method proceeds to block 216.

At block 216, the computing device obtains the requested information. In some embodiments, the computing device obtains the requested information directly from one or more components of the computing device (e.g., a microphone of the computing device, a camera of the computing device, etc.). In other embodiments, the computing device obtains the requested information from another device in communication with the computing device (e.g., a responder device). At block 218, the computing device sends the obtained information to the dispatch computing device. In one embodiment, the computing device sends the obtained information to the dispatch computing device via the same network as the computing device that sent the indication of the particular event in block 208. In another embodiment, the computing device sends the obtained information to the dispatch computing device via a different network than the computing device that sent the indication of the particular event in block 208, such as in an example where the indication of the particular event is sent via a cellular network (e.g., 4G, LTE) and the obtained information is sent via another network (e.g., WiFi). After the computing device sends the obtained information to the dispatch computing device at block 218, the method returns back to block 202 to monitor for additional inputs.

Figure 4A:
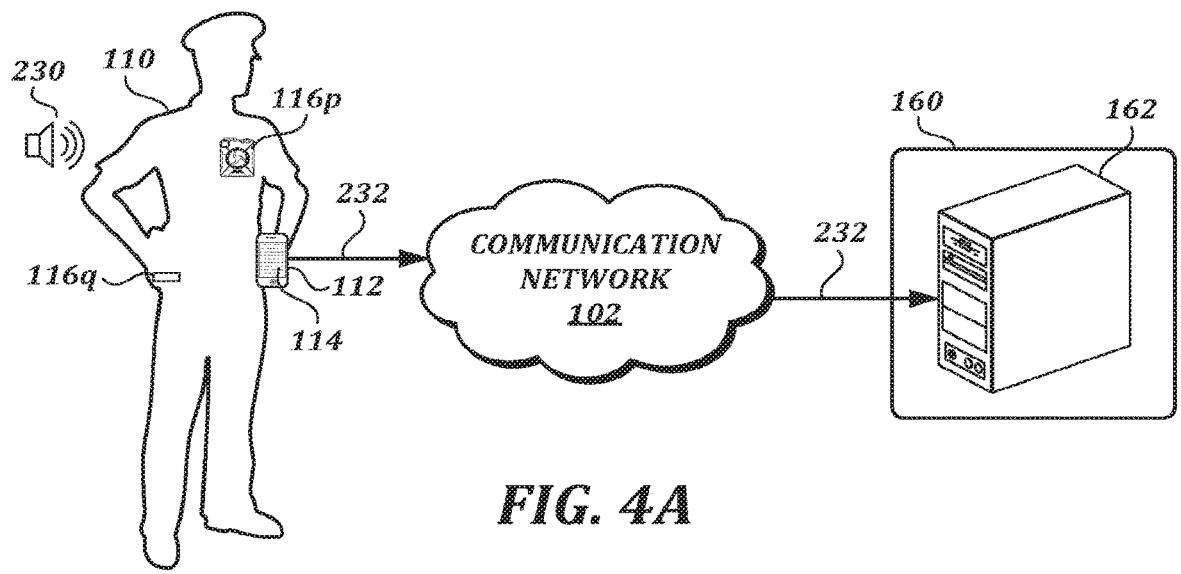
FIGS. 4A to 4C depict an embodiment of execution of the method 200 depicted in FIG. 3, in accordance with embodiments of computing devices disclosed herein.
Figure 4B:
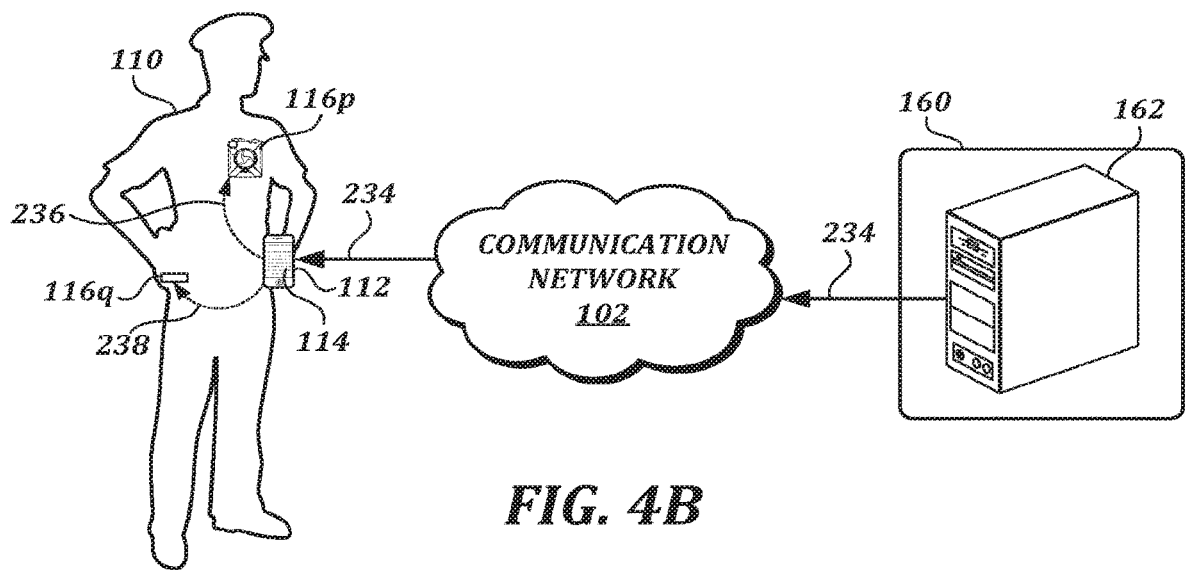
Figure 4C:
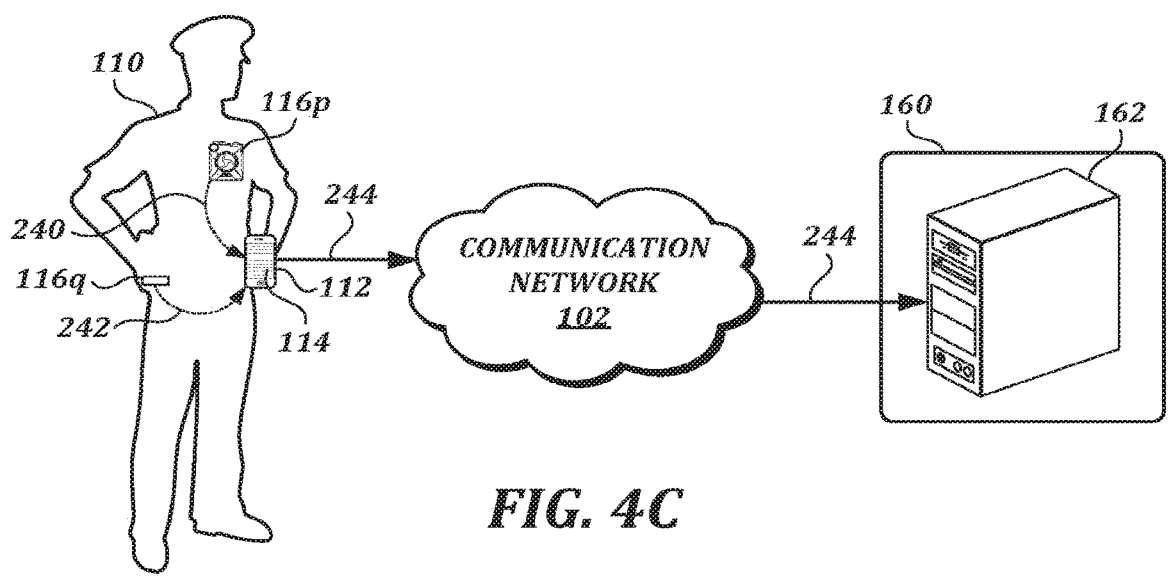

An embodiment of execution of the method 200 depicted in FIG. 3 is depicted in FIGS. 4A to 4C. In FIGS. 4A to 4C, the responder 110 has the computing device 112 with the communications application 114. The computing device 112 is in communication with the dispatch unit computing device 162 at the dispatch unit 160 via the network 102. The responder also has a body camera 116p and a holster sensor 116q that are in communication with the computing device 112. In one embodiment, the body camera 116p is any wearable camera that can capture images and/or video while being worn by the responder 110. In one embodiment, the communications application 114 includes instructions that, in response to execution by the computing device 112, cause the computing device 112 to perform the method 200 depicted in FIG. 3.

In the embodiment depicted in FIG. 4A, the computing device 112 monitors for inputs and receives an input in the form of a sound 230. The computing device interprets the sound 230 as the sound of a gunshot and sends an indication 232 that a gunshot has occurred to the dispatch unit computing device 162 via the network 102.

In the embodiment depicted in FIG. 4B, the dispatch unit computing device 162 sends a request 234 for information to the computing device 112 via the network 102. The request 234 for information includes a request for live video and for the status of the responder's holster. The computing device 112 receives the request 234 for information and sends signals 236 and 238, respectively, to the body camera 116p and the holster sensor 116q. Optionally, the signals 236 and 238 enable the body camera 116p and the holster sensor 116q, respectively. The signals 236 and 238 cause the body camera 116p and the holster sensor 116q, respectively, to provide live streaming video and holster status information to the computing device 112.

In the embodiment depicted in FIG. 4C, the body camera 116p and the holster sensor 116q send, respectively, live video 240 and holster status information 242 to the computing device 112. The computing device 112 obtains the live video 240 and the holster status information 242 from the body camera 116p and the holster sensor 116q and sends the requested information 244 to the dispatch unit computing device 162 via the network 102.

In one example of the embodiment depicted in FIGS. 4A to 4C, the sound 230 is the sound of a car backfiring, but the computing device 112 determines that the sound 230 is a gunshot. In this example where the sound 230 is the sound of a car backfiring, a dispatcher at the dispatch unit may view the live video 240 indicating a non-emergency situation and the holster status information 242 indicating that the holster is closed. The dispatcher may then deem the situation to be normal and contact the responder 110 (e.g., a radio communication system) when convenient to ensure that the situation is normal. In another example of the embodiment depicted in FIGS. 4A to 4C, the sound 230 is the sound of a gunshot and the computing device 112 determines that the sound 230 is a gunshot. In this example where the sound 230 is the sound of a a gunshot, a dispatcher at the dispatch unit may view the live video 240 indicating that the responder 110 is running and the holster status information 242 indicating that the holster is open. The dispatcher may then deem the situation to be an emergency and that additional responders need to be dispatched to the location of the responder 110. The embodiment depicted in FIGS. 4A to 4C allows the dispatcher to dispatch additional responders without the responder 110 sending a radio communication to the dispatch unit 160.

Figure 5A:
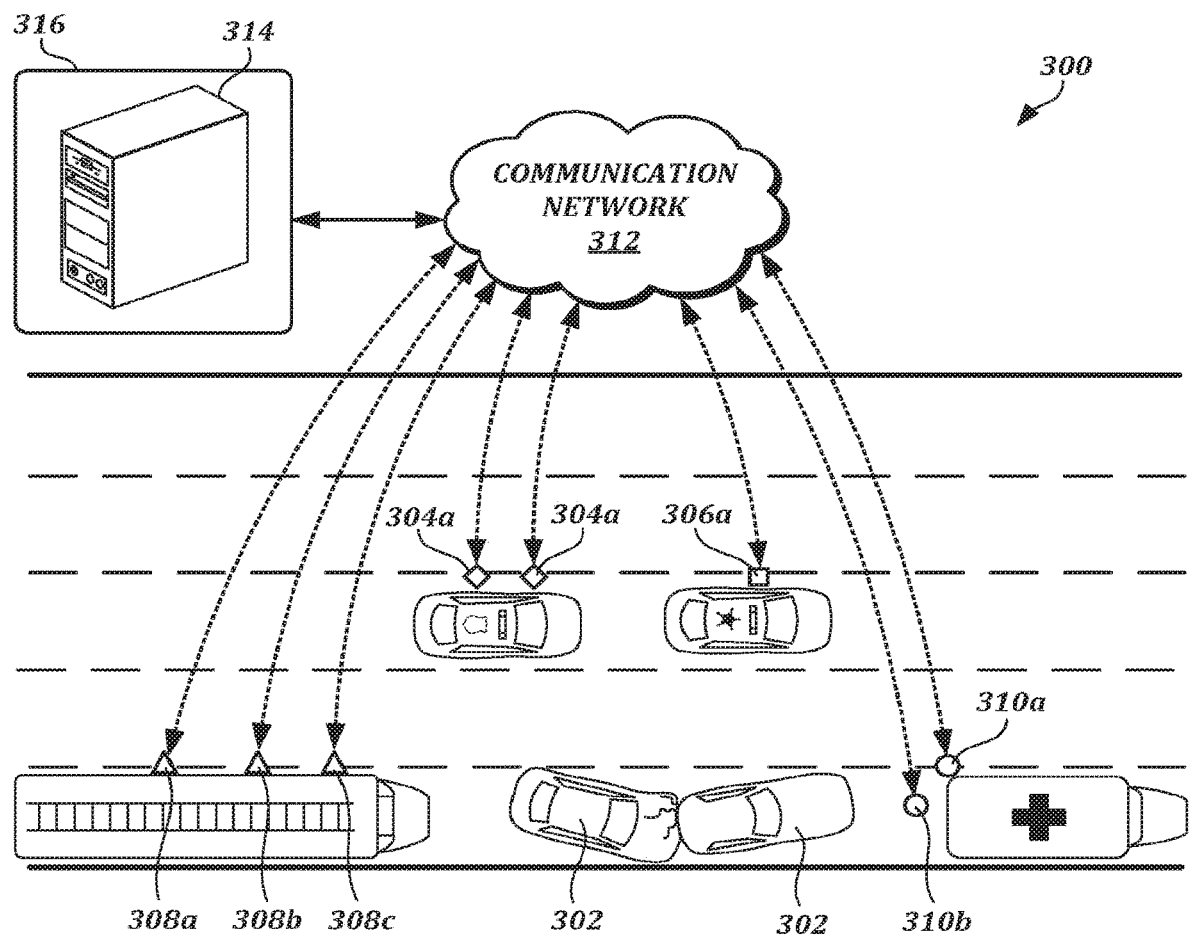
FIGS. 5A and 5B depict an embodiment of a dispatch computing device managing responders at a location or event, in accordance with embodiments of computing devices disclosed herein.
Figure 5B:
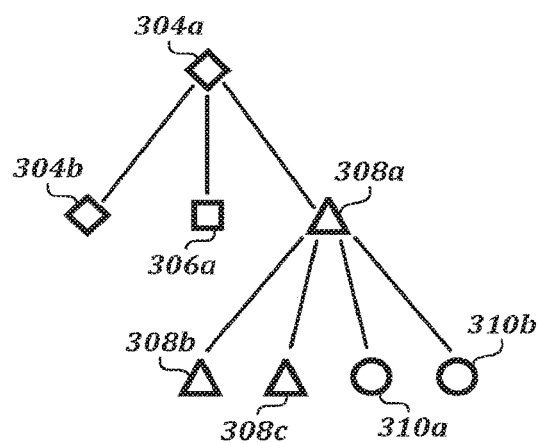

In other embodiments, a dispatch computing device manages multiple responders by communicating with computing devices of the responders. FIGS. 5A and 5B depict an embodiment of a dispatch computing device managing responders at a location or event. In the embodiment of the location 300 depicted in FIG. 5A, a car collision 302 has occurred. Multiple responders are responding to the car collision 302, including police officers 304a-b, highway patrol officer 306a, fire fighters 308a-c, and paramedics 310a-b. Each of the police officers 304a-b, the highway patrol officer 306a, the fire fighters 308a-c, and the paramedics 310a-b has a computing device (e.g., computing devices 112, 122, 132, 142, and 152). Each of the responders' computing devices is in communication with a network 312. A dispatch computing device 314 is located in a dispatch unit 316 that is remote from the location 300 of the car collision 302. The dispatch computing device 314 is in communication with the network 312.

In one embodiment, the dispatch computing device 314 determines that the computing devices of the police officers 304a-b, the highway patrol officer 306a, the fire fighters 308a-c, and the paramedics 310a-b are located in proximity to the location 300 and/or the car collision 302 (i.e., an event). In one example, the computing devices of the police officers 304a-b, the highway patrol officer 306a, the fire fighters 308a-c, and the paramedics 310a-b periodically send indications of their locations to the dispatch computing device 314 via the network 312 and the dispatch computing device 314 determines the proximity of the computing devices to the location or event based on the last-reported location of each computing device. In another example, the dispatch computing device 314 requests that computing devices of responders in communication with the network 312 report their location prior to the dispatch computing device 314 determining which computing devices are in proximity to the location or event.

In another embodiment, the dispatch computing device 314 determines a hierarchy of the police officers 304a-b, the highway patrol officer 306a, the fire fighters 308a-c, and the paramedics 310a-b in proximity to the car collision 302. One example of a hierarchy determined by the dispatch computing device 314 is depicted in FIG. 5B. In the depicted embodiment, the police officer 304a is at the top level of the hierarchy. The police officer 304b, the highway patrol officer 306a, and the fire fighter 308a are at the second level of the hierarchy and report to the police officer 304a. The fire fighters 308b-c and the paramedics 310a-b are at the third level of the hierarchy and report to the fire fighter 308a. In some embodiments, the determined hierarchy is based on one or more of a seniority of the responders at the location, a task occurring at the particular location, a responder agency associated with each of the responders, and the like.

The dispatch computing device 314 sends an indication of the hierarchy to each of the computing devices of the police officers 304a-b, the highway patrol officer 306a, the fire fighters 308a-c, and the paramedics 310a-b. The computing devices of the police officers 304a-b, the highway patrol officer 306a, the fire fighters 308a-c, and the paramedics 310a-b are configured to communicate with each other via an established communication link (e.g., via the network 312) based on the hierarchy received from the dispatch computing device. For example, using the hierarchy depicted in FIG. 5B, communications from the computing device of the police officer 304a are given the highest priority among communications between the police officers 304a-b, the highway patrol officer 306a, the fire fighters 308a-c, and the paramedics 310a-b. In one example, an audio message communication by the police officer 304a (e.g., a live audio voice message) via the communication link interrupts any other audio message communication sent by one of the police officer 304b, the highway patrol officer 306a, the fire fighters 308a-c, and the paramedics 310a-b.

The creation and transmission of the hierarchy of responders allows a dispatch unit to create the hierarchy and inform the responder computing devices of the hierarchy without input from responders. This allows the responders to focus on the tasks they are doing without first taking time to establish a hierarchy of those responders at the location or event. This creation of the hierarchy and informing the responder computing devices of the hierarchy may especially be helpful when responders from different responder agencies (e.g., police officers from a police department, fire fighters from a fire department, etc.) are at a particular location or event. Similarly, the creation of the hierarchy and informing the responder computing devices of the hierarchy may be helpful when responders from different organizations of a responder agency (e.g., fire fighters from one fire house of a fire department and fire fighters from another fire house of the fire department, police officers from a police department and detectives from the police department, etc.) are at a particular location or event.

In some embodiments, once a communication link has been established among the police officers 304a-b, the highway patrol officer 306a, the fire fighters 308a-c, and the paramedics 310a-b, a subset of those responders may be selected for sending specific information. In one example, the dispatch computing device 314 receives an indication from the dispatcher of a subset of the police officers 304a-b, the highway patrol officer 306a, the fire fighters 308a-c, and the paramedics 310a-b that includes the fire fighters 308a-c and the paramedics 310a-b and the dispatch computing device 314 sends information to that subset of responders. Such a subset may be useful for sending information related to medical care of people in the car collision 302, such as availability of local hospitals, medical information about the people in the car collision 302, etc. In another example, the dispatch computing device 314 receives an indication of a subset of the police officers 304a-b, the highway patrol officer 306a, the fire fighters 308a-c, and the paramedics 310a-b that includes the police officer 304a and the fire fighter 308a, and the dispatch computing device 314 sends information to that subset of responders. Such a subset may be useful for sending information related to those responders that oversee other responders at the location 300 of the car collision 302.

Figure 6:
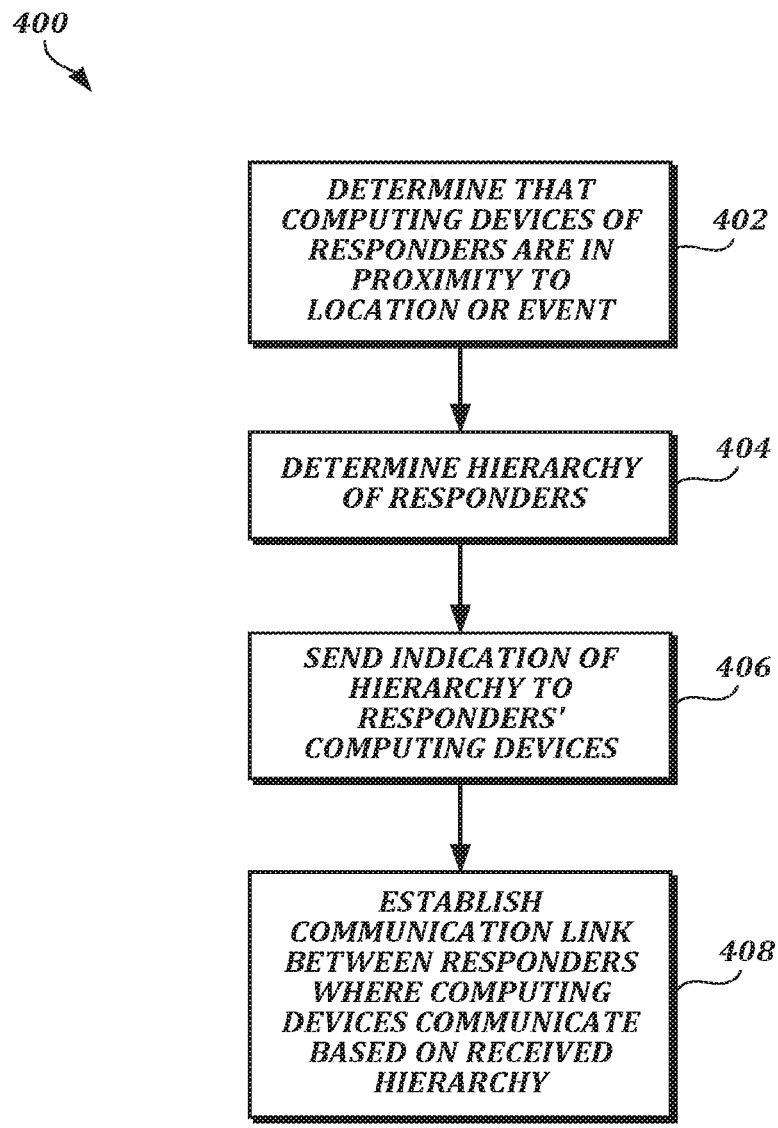
FIG. 6 depicts an embodiment of a method performed by a dispatch computing device to manage a plurality of responders, in accordance with embodiments of computing devices disclosed herein.

An embodiment of a method 400 performed by dispatch computing device (e.g., dispatch computing device 314) to manage a plurality of responders is depicted in FIG. 6. At block 402, the dispatch computing device determines that the computing devices of the plurality of responders are located in proximity to a location or event. In some embodiments, the responders in the plurality of responders are from the same responder agency, from different responder agencies, from different organizations of a responder agency, and the like. At block 404, the dispatch computing device determines a hierarchy of the plurality of responders. In some embodiments, the determined hierarchy is based on one or more of a seniority of the responders at the location, a task occurring at the particular location, a responder agency associated with each of the responders, and the like.

At block 406, the dispatch computing device sends an indication of the hierarchy to computing devices of each of the plurality of responders. In one example, the dispatch computing device sends the indication of the hierarchy via a network, such as a cellular network, a WiFi network, a local area network, any other network, or any combination thereof. At block 408, the dispatch computing device establishes a communication link between the computing devices of the plurality of responders where the computing devices of the plurality of responders are configured to communicate with each other via the communication link based on the hierarchy received from the dispatch computing device. In some embodiments, the computing devices of the plurality of responders communicate with each other via the communication link based on the hierarchy by giving priority to communications received from computing devices of responders that are higher in the hierarchy. In some embodiments, the communication links described herein are peer-to-peer communication links. In other embodiments, the communication links described herein are server-mediated communication links. In other embodiments, the communication links described herein use one or more protocols, such as the internet protocol, mobile telephony protocols, push-to-talk over cellular protocols, and the like.

Figure 7:
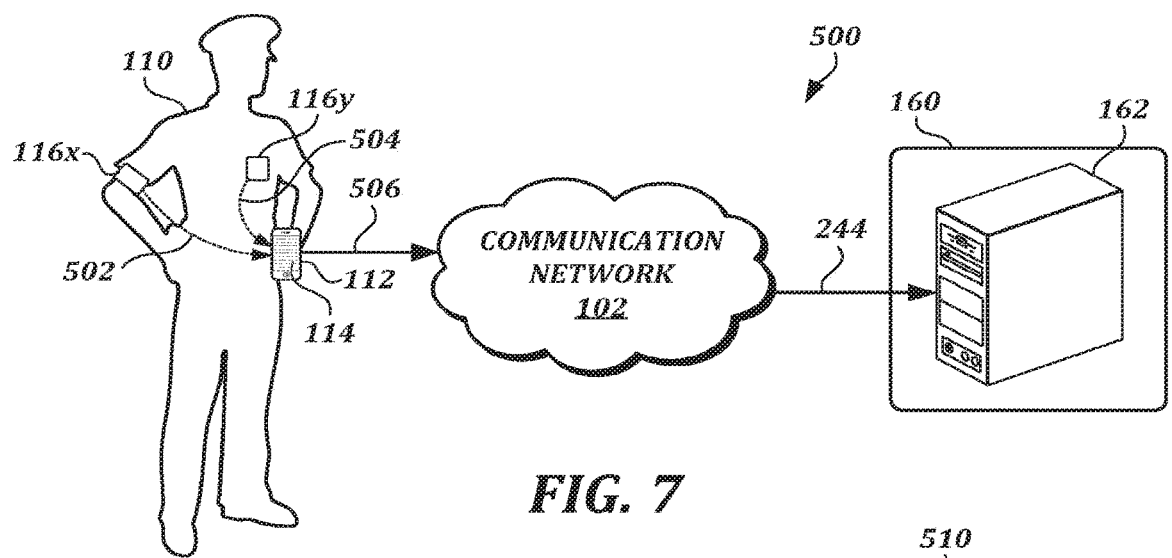
FIG. 7 depicts an embodiment of a system for providing biometric data to a dispatch computing device, in accordance with embodiments of computing devices disclosed herein.

In some embodiments, management of responders by a dispatch computing device is aided by biometric data about the responders. FIG. 7 depicts an embodiment of a system 500 for providing biometric data to a dispatch computing device. In the depicted embodiment, the responder 110 has the computing device 112 with the communications application 114. The computing device 112 is in communication with the dispatch computing device 162 at the dispatch unit 160 via the network 102. The responder also has a blood pressure monitor 116x and a heart rate monitor 116y that are in communication with the computing device 112. The blood pressure monitor 116x is configured to generate a signal indicative of a blood pressure of the responder 110 and the heart rate monitor 116y is configured to generate a signal indicative of a heart rate of the responder 110. While the particular embodiment shown in FIG. 7 includes the blood pressure monitor 116x and the heart rate monitor 116y, other embodiments may include one or more biometric data sensors, such as one or more of a blood pressure monitor, a heart rate monitor, a blood flow monitor, a blood oxygen level monitor, a respiratory rate monitor, a brain wave monitor, body temperature monitor, and the like.

The computing device 112 receives a blood pressure signal 502 from the blood pressure monitor 116x and a heart rate signal 504 from the heart rate monitor 116y. The computing device 112 sends biometric data 506 to the dispatch computing device 162 via the network 102. The biometric data 506 includes indications of the blood pressure signal 502 and the heart rate signal 504 received from the blood pressure monitor 116x and the heart rate monitor 116y, respectively. In one embodiment, the communications application 114 includes instructions that, in response to execution by the computing device 112, cause the computing device 112 to obtain the blood pressure signal 502 and the heart rate signal 504 and to send the biometric data 506. In some embodiments, the computing device 112 sends the biometric data 506 to the dispatch computing device 162 on a periodic basis, when requested by the dispatch computing device 162, when requested by a user input to the computing device 112, or any combination thereof.

Figure 8A:
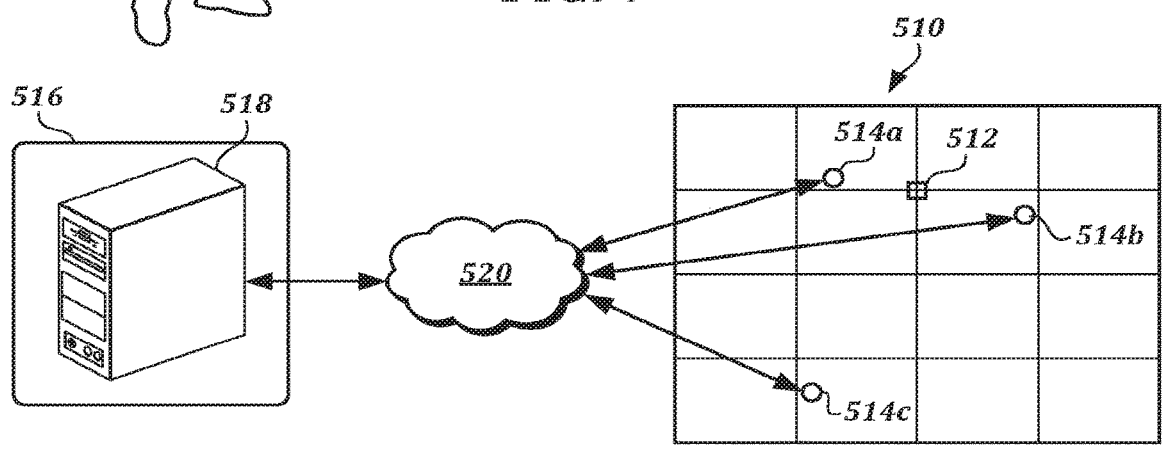
FIGS. 8A and 8B depict an embodiment of a dispatch computing device using biometric data about responders to manage the responders, in accordance with embodiments of computing devices disclosed herein.
Figure 8B:
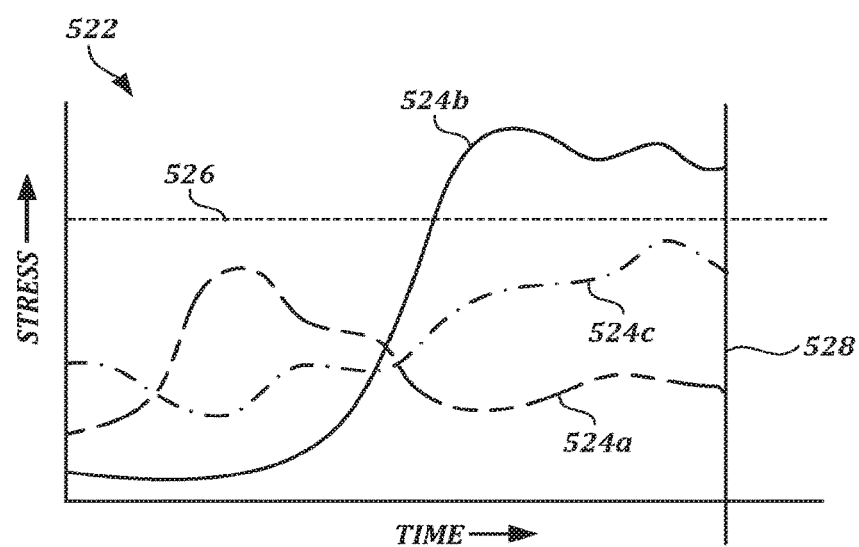

An embodiment of a dispatch computing device using biometric data about responders to manage the responders is depicted in FIGS. 8A and 8B. In the embodiment shown in FIG. 8A, a map 510 depicts a location of an incident 512 and locations of responders 514a-c. Each of the responders 514a-c has a computing device. Also depicted is a dispatch unit 516 that includes a dispatch computing device 518. Each of the computing devices of the responders 514a-c and the dispatch computing device 518 of the dispatch unit 516 is in communication with a network 520.

In one embodiment, the computing devices of the responders 514a-c obtain biometric data about the responders 514a c and send the biometric data to the dispatch computing device 518 via the network 520. In some examples, the computing devices of the responders 514a-c send the biometric data to the dispatch computing device 518 on a periodic basis, in response to a request from the dispatch computing device 518, in response to a user input on the computing devices, or at any other time. In one embodiment, the dispatch computing device 518 determines a stress level of each of the responders 514a c based on the biometric data received from the computing devices of the responders 514a c.

In one embodiment depicted in FIG. 8B, the dispatch computing device 518 maintains a chart 522 of stress levels of the responders 514a c over time. More specifically, the chart 522 includes indication of stress levels 524a-c corresponding to the responders 514a c, respectively. The chart 522 in FIG. 8B also includes a stress threshold level 526. In some embodiments, responders are dispatched based on a level of stress of the responders against the stress threshold level 526. For example, at the time 528 depicted in FIG. 8B, a dispatcher determines to dispatch two responders to the incident 512 depicted in FIG. 8A. As shown in FIG. 8A, responders 514a and 514b are the closest responders to the incident. However, as shown in FIG. 8B, the stress level 524b of the responder 514b is above the stress threshold level 526 at the time 528 that the dispatcher is dispatching officers to the incident 512. In this case, the dispatcher determines to dispatch responders 514a and 514c to the incident because, even though responder 514b is closer to the incident than the responder 514c, the respective stress levels 524a and 524c of the responders 514a and 514c are below the stress threshold level 526 at the time 528. In one embodiment, the dispatch computing device 518 displays the chart 522 or some other indication of the stress level of the responders 514a-c to a dispatcher on a display device to aid the dispatcher in making decisions about dispatch of the officers 514a-c.

Figure 9:
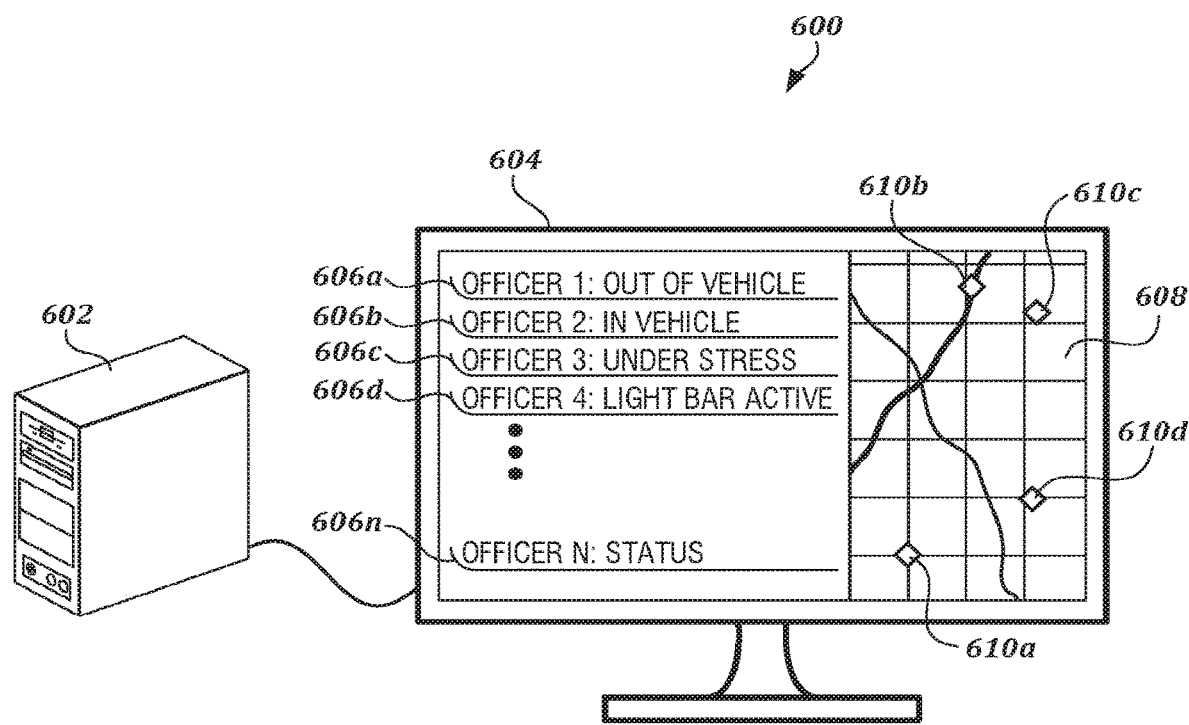
FIG. 9 depicts an embodiment of a system that displays information for use by a dispatcher, in accordance with embodiments of computing devices disclosed herein.

Another embodiment of a system 600 that displays information for use by a dispatcher is depicted in FIG. 9. The system 600 includes a dispatch computing device 602 coupled to a display device 604. In some examples, the display device 604 includes one or more of a monitor, a television, a touchscreen display, a projector, or any other display device. In one embodiment, the dispatch computing device 602 receives information from computing devices of a number of responders. In some embodiments, the information received by the dispatch computing device 602 from the responder computing devices includes one or more of location information, biometric information, responder device status information, and the like.

In one embodiment, the dispatch computing device 602 includes instructions that, in response to being executed by the dispatch computing device 602, cause the dispatch computing device 602 to display, on the display device 604, status listings 606a-n. The status listings 606a-n include a status of each of a plurality of responders. In some embodiments, the status listings 606a-n include at least one of an indication of whether the responder is in or out of a vehicle, an indication of a stress level of the responder, an indication of whether a light bar of the responder's vehicle is active, an indication of the responder's availability to respond to an incident, or any other information. In some embodiments, the status listings 606a-n are colored based on the statuses of the responders (e.g., green for available, orange for under stress, red if a weapon is drawn, blue if a light bar is active, etc.). Coloring status listings 606a-n may aid a dispatcher in quickly determining the statuses of the responders.

In another embodiment, as depicted in FIG. 9, the dispatch computing device 602 causes the display device 604 to display a map 608 at the same time as the status listings 606a-n are displayed. The map 608 includes indications 610a-d of locations of computing devices of responders. In one example, the indications 610a-d of locations of computing devices of responders correspond, respectively, with the status listings 606a-d of responders. Such a display on the display device 604 may allow a dispatcher to quickly determine how to dispatch responders based on a combination of location and status. While the display device 604 depicted in FIG. 9 is a single display device, in other embodiments, the computing device displays information on multiple display devices (e.g., the status listings 606a-n depicted on a first display device and the map 608 depicted on a second display device).

Figure 10A:
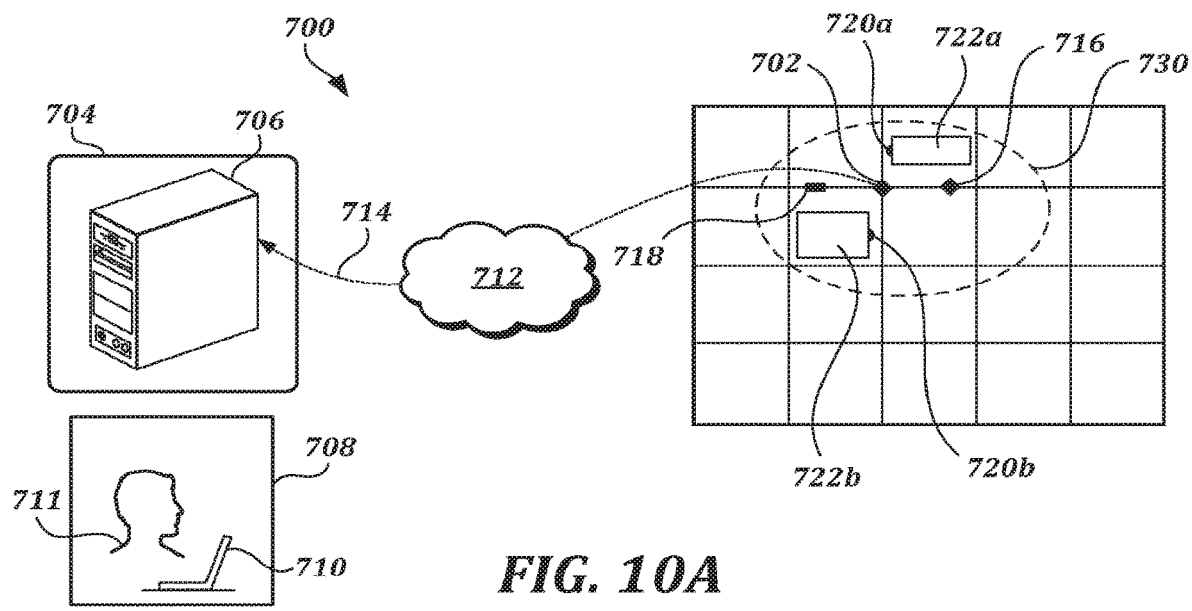
FIGS. 10A to 10C depict an embodiment of a dispatch computing device used to manage responders, in accordance with embodiments of computing devices disclosed herein.
Figure 10B:
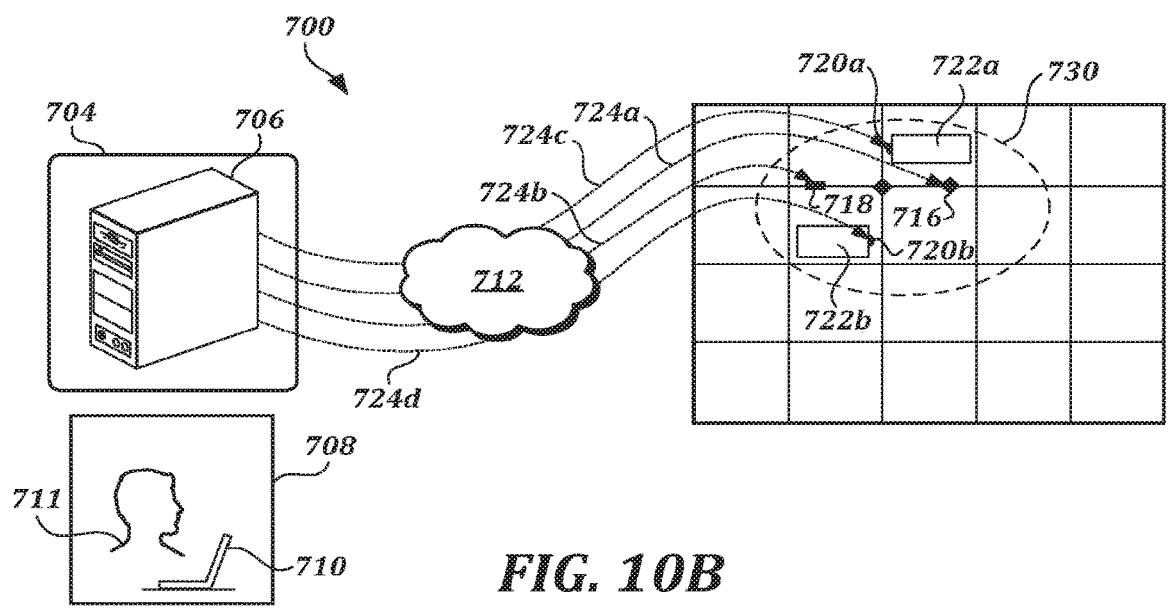
Figure 10C:
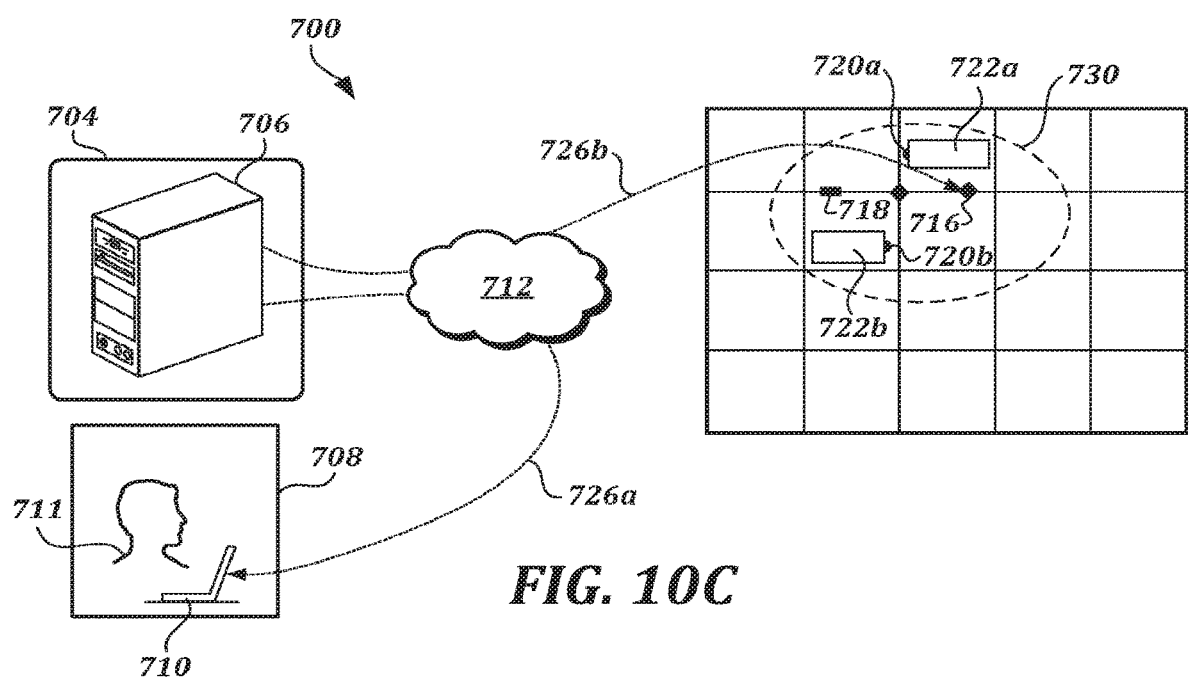

Another embodiment of a dispatch computing device used to manage responders is depicted in FIGS. 10A to 10C. Depicted in FIGS. 10A to 10C is a map 700 with an indication of a location of a responder 702, a dispatch unit 704 with a dispatch computing device 706, a remote location 708 with a computing device 710 and a responder 711. The responder 702 has a computing device. The computing device of the responder 702, the dispatch computing device 706, and the computing device 710 are configured to communicate with each other via the network 712. In the particular example depicted herein the responder 711 is a supervisor of the responder 702.

In the embodiment depicted in FIG. 10A, the first responder 702 sends a request 714 from the computing device of the responder 702 to the dispatch computing device 706 via the network. In this particular embodiment, the request 714 is a request to activate cameras within a geographic range 730. In the example shown in FIG. 10A, the geographic range 730 is defined by a particular radius around the responder 702. A number of cameras are located within the geographic range 730, including a body camera 716 on a responder, a dash camera 718 in a responder vehicle, and security cameras 720*a-b* on buildings 722*a-b*. In one embodiment, the body camera 716, the dash camera 718, and the security cameras 720*a-b* are all of the cameras that can be activated by the dispatch computing device 706, but they may not be the only cameras within the geographic range.

In the embodiment shown in FIG. 10B, the dispatch computing device 706 sends activation signals 724*a-d* to the body camera 716, the dash camera 718, and the security cameras 720*a-b* via the network 712. Each of the body camera 716, the dash camera 718, and the security cameras 720*a-b* is configured to activate and begin streaming video in response to receiving one of the activation signals 724*a-d*. In one embodiment, the body camera 716, the dash camera 718, and the security cameras 720*a-b* stream video back to the dispatch computing device 706 and the dispatch computing device 706 sends one or more of the video stream to the computing device of the responder 702. In another embodiment, the body camera 716, the dash camera 718, and the security cameras 720*a-b* stream video directly to the computing device of the responder 702. In both embodiments, the responder 702 receives streamed video from one or more of the cameras within the geographic area 730, which permits the responder 702 to see events happening in other areas within the geographic area 730.

In the embodiment shown in FIG. 10C, the dispatch computing device 706 sends a notification 726*a* to the computing device 710 via the network 712. The notification 726*a* is sent in response to the dispatch computing device 706 receiving the request 714 from the computing device of the responder 702. The notification 726*a* informs the supervisory responder 711 that the responder 702 requested activation of cameras in the geographic range 730. In one embodiment, the notification 726*a* includes a video stream of the cameras requested by the responder 702. In the embodiment shown in FIG. 10C, the dispatch computing device 706 also sends a notification 726*b* to a computing device of the responder associated with body camera 716 via the network 712. The notification 726*b* is sent in response to the dispatch computing device 706 receiving the request 714 from the computing device of the responder 702. The notification 726*b* informs the responder that the responder 702 requested activation of cameras in the geographic range 730. In one embodiment, the notification 726*b* includes a video stream of the cameras requested by the responder 702. In the case where the responder associated with the body camera 716 is a partner of the responder 702, the sending of the request 714 by the responder 702 results in the notification 726*b* being sent to the partner of the responder 702. The notification 726*b* may signal that the responder 702 requires assistance even if the responder 702 and the partner of the responder 702 are not close enough to see or speak to each other.

Unless otherwise specified in the context of specific examples, described techniques and tools may be implemented by any suitable computing device or set of computing devices.

In any of the described examples, a data store contains data as described herein and may be hosted, for example, by a database management system (DBMS) to allow a high level of data throughput between the data store and other components of a described system. The DBMS may also allow the data store to be reliably backed up and to maintain a high level of availability. For example, a data store may be accessed by other system components via a network, such as a private network in the vicinity of the system, a secured transmission channel over the public Internet, a combination of private and public networks, and the like. Instead of or in addition to a DBMS, a data store may include structured data stored as files in a traditional file system. Data stores may reside on computing devices that are part of or separate from components of systems described herein. Separate data stores may be combined into a single data store, or a single data store may be split into two or more separate data stores.

Some of the functionality described herein may be implemented in the context of a client-server relationship. In this context, server devices may include suitable computing devices configured to provide information and/or services described herein. Server devices may include any suitable computing devices, such as dedicated server devices. Server functionality provided by server devices may, in some cases, be provided by software (e.g., virtualized computing instances or application objects) executing on a computing device that is not a dedicated server device. The term "client" can be used to refer to a computing device that obtains information and/or accesses services provided by a server over a communication link. However, the designation of a particular device as a client device does not necessarily require the presence of a server. At various times, a single device may act as a server, a client, or both a server and a client, depending on context and configuration. Actual physical locations of clients and servers are not necessarily important, but the locations can be described as "local" for a client and "remote" for a server to illustrate a common usage scenario in which a client is receiving information provided by a server at a remote location.

Figure 11:
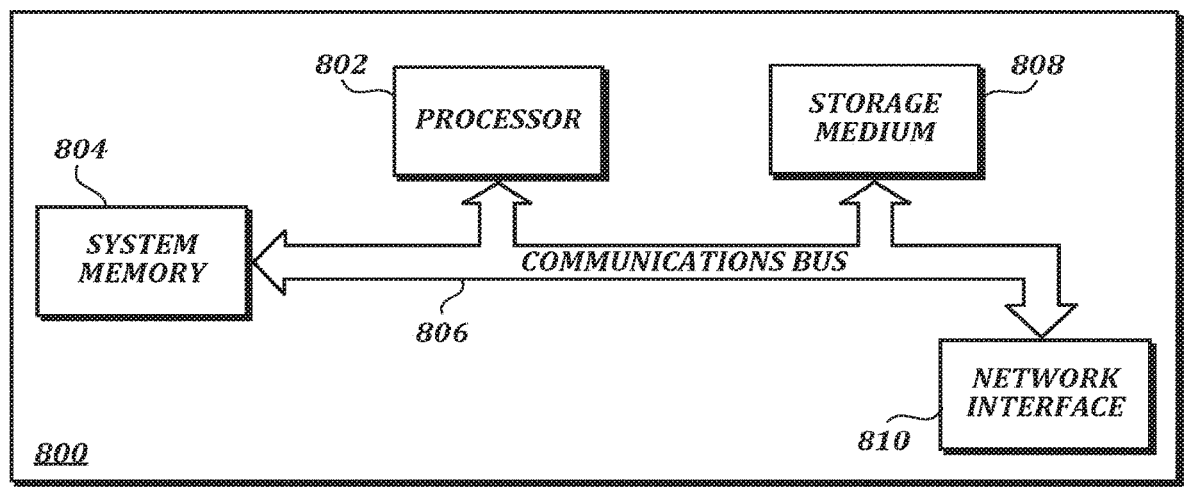
FIG. 11 depicts a block diagram that illustrates aspects of an illustrative computing device appropriate for use in accordance with embodiments of the present disclosure.

FIG. 11 depicts a block diagram that illustrates aspects of an illustrative computing device 800 appropriate for use in accordance with embodiments of the present disclosure. The description below is applicable to servers, personal computers, mobile phones, smart phones, tablet computers, embedded computing devices, and other currently available or yet to be developed devices that may be used in accordance with embodiments of the present disclosure.

In its most basic configuration, the computing device 800 includes at least one processor 802 and a system memory 804 connected by a communication bus 806. Depending on the exact configuration and type of device, the system memory 804 may be volatile or nonvolatile memory, such as read only memory ("ROM"), random access memory ("RAM"), EEPROM, flash memory, or other memory technology. Those of ordinary skill in the art and others will recognize that system memory 804 typically stores data and/or program modules that are immediately accessible to and/or currently being operated on by the processor 802. In this regard, the processor 802 may serve as a computational center of the computing device 800 by supporting the execution of instructions.

As further illustrated in FIG. 11, the computing device 800 may include a network interface 810 comprising one or more components for communicating with other devices over a network. Embodiments of the present disclosure may access basic services that utilize the network interface 810 to perform communications using common network protocols. The network interface 810 may also include a wireless network interface configured to communicate via one or more wireless communication protocols, such as WiFi, 2G, 3G, 4G, LTE, WiMAX, Bluetooth, and/or the like.

In the illustrative embodiment depicted in FIG. 11, the computing device 800 also includes a storage medium 808. However, services may be accessed using a computing device that does not include means for persisting data to a local storage medium. Therefore, the storage medium 808 depicted in FIG. 11 is optional. In any event, the storage medium 808 may be volatile or nonvolatile, removable or non-removable, implemented using any technology capable of storing information such as, but not limited to, a hard drive, solid state drive, CD ROM, DVD, or other disk storage, magnetic tape, magnetic disk storage, and/or the like.

As used herein, the term "computer readable medium" includes volatile and nonvolatile and removable and non-removable media implemented in any method or technology capable of storing information, such as computer readable instructions, data structures, program modules, or other data. In this regard, the system memory 804 and storage medium 808 depicted in FIG. 11 are examples of computer readable media.

For ease of illustration and because it is not important for an understanding of the claimed subject matter, FIG. 11 does not show some of the typical components of many computing devices. In this regard, the computing device 800 may include input devices, such as a keyboard, keypad, mouse, trackball, microphone, video camera, touchpad, touchscreen, electronic pen, stylus, and/or the like. Such input devices may be coupled to the computing device 800 by wired or wireless connections including RF, infrared, serial, parallel, Bluetooth, USB, or other suitable connection protocols using wireless or physical connections.

In any of the described examples, data can be captured by input devices and transmitted or stored for future processing. The processing may include encoding data streams, which can be subsequently decoded for presentation by output devices. Media data can be captured by multimedia input devices and stored by saving media data streams as files on a computer readable storage medium (e.g., in memory or persistent storage on a client device, server, administrator device, or some other device). Input devices can be separate from and communicatively coupled to computing device 800 (e.g., a client device), or can be integral components of the computing device 800. In some embodiments, multiple input devices may be combined into a single, multifunction input device (e.g., a video camera with an integrated microphone). The computing device 800 may also include output devices such as a display, speakers, printer, etc. The output devices may include video output devices such as a display or touchscreen. The output devices also may include audio output devices such as external speakers or earphones. The output devices can be separate from and communicatively coupled to the computing device 800, or can be integral components of the computing device 800. Input functionality and output functionality may be integrated into the same input/output device (e.g., a touchscreen). Any suitable input device, output device, or combined input/output device either currently known or developed in the future may be used with described systems.

In general, functionality of computing devices described herein may be implemented in computing logic embodied in hardware or software instructions, which can be written in a programming language, such as C, C++, COBOL, JAVA™, PHP, Perl, Python, Ruby, HTML, CSS, JavaScript, VBScript, ASPX, Microsoft.NET™ languages such as C#, and/or the like. Computing logic may be compiled into executable programs or written in interpreted programming languages. Generally, functionality described herein can be implemented as logic modules that can be duplicated to provide greater processing capability, merged with other modules, or divided into sub modules. The computing logic can be stored in any type of computer readable medium (e.g., a non-transitory medium such as a memory or storage medium) or computer storage device and be stored on and executed by one or more general purpose or special purpose processors, thus creating a special purpose computing device configured to provide functionality described herein.

Many alternatives to the systems and devices described herein are possible. For example, individual modules or subsystems can be separated into additional modules or subsystems or combined into fewer modules or subsystems. As another example, modules or subsystems can be omitted or supplemented with other modules or subsystems. As another example, functions that are indicated as being performed by a particular device, module, or subsystem may instead be performed by one or more other devices, modules, or subsystems. Although some examples in the present disclosure include descriptions of devices comprising specific hardware components in specific arrangements, techniques and tools described herein can be modified to accommodate different hardware components, combinations, or arrangements. Further, although some examples in the present disclosure include descriptions of specific usage scenarios, techniques and tools described herein can be modified to accommodate different usage scenarios. Functionality that is described as being implemented in software can instead be implemented in hardware, or vice versa.

Many alternatives to the techniques described herein are possible. For example, processing stages in the various techniques can be separated into additional stages or combined into fewer stages. As another example, processing stages in the various techniques can be omitted or supplemented with other techniques or processing stages. As another example, processing stages that are described as occurring in a particular order can instead occur in a different order. As another example, processing stages that are described as being performed in a series of steps may instead be handled in a parallel fashion, with multiple modules or software processes concurrently handling one or more of the illustrated processing stages. As another example, processing stages that are indicated as being performed by a particular device or module may instead be performed by one or more other devices or modules.

Embodiments disclosed herein include a computer-implemented method for performing one or more of the above-described techniques; a computing device comprising a processor and computer readable storage media having stored thereon computer-executable instructions configured to cause the server computer to perform one or more of the above described techniques; a computer readable storage medium having stored thereon computer-executable instructions configured to cause a computing device to perform one or more of the above-described techniques; a computing system comprising a server that provides one or more of the above-described services. The computer system may further comprise plural client computing devices; and a client computing device in communication with a server that provides one or more of the above-described services, the client computing device comprising a processing unit and computer readable storage media having stored thereon computer-executable instructions configured to cause the client computing device to perform one or more of the above described techniques.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the claimed subject matter.

While illustrative embodiments have been illustrated and described, it will be appreciated that various changes can be made therein without departing from the spirit and scope of the claimed subject matter.

The foregoing description discusses preferred embodiments of the present invention, which may be changed or modified without departing from the scope of the present invention as defined in the claims. Examples listed in parentheses may be used in the alternative or in any practical combination. As used in the specification and claims, the words 'comprising', 'comprises', 'including', 'includes', 'having', and 'has' introduce an open ended statement of component structures and/or functions. In the specification and claims, the words 'a' and 'an' are used as indefinite articles meaning 'one or more'. When a descriptive phrase includes a series of nouns and/or adjectives, each successive word is intended to modify the entire combination of words preceding it. For example, a black dog house is intended to mean a house for a black dog. While for the sake of clarity of description, several specific embodiments of the invention have been described, the scope of the invention is intended to be measured by the claims as set forth below. In the claims, the term "provided" is used to definitively identify an object that not a claimed element of the invention but an object that performs the function of a workpiece that cooperates with the claimed invention. For example, in the claim "an apparatus for aiming a provided barrel, the apparatus comprising: a housing, the barrel positioned in the housing", the barrel is not a claimed element of the apparatus, but an object that cooperates with the "housing" of the "apparatus" by being positioned in the "housing". The invention includes any practical combination of the structures and methods disclosed. While for the sake of clarity of description several specifics embodiments of the invention have been described, the scope of the invention is intended to be measured by the claims as set forth below.

What is claimed is:

1. A first computing device of a responder for automatically communicating with a remote second computing device during an event associated with the responder, the first computing device comprising:
a microphone;
a camera;
a processor; and
a memory having instructions stored thereon, the instructions in response to execution by the processor cause the first computing device to:
determine that the event associated with the responder has occurred;
automatically send an indication of the event to the remote second computing device in response to determining that the event has occurred;
receive, from the remote second computing device, a request for information, wherein the request for information is received after automatically sending the indication of the event to the remote second computing device, and wherein the request for information includes a request for an information requested by the remote second computing device;
obtain the information requested by the remote second computing device; and
send the information requested by the remote second computing device, wherein the information requested by the remote second computing device is obtained directly from one or more of the microphone of the first computing device and the camera of the first computing device.

2. The first computing device of claim 1 wherein the information requested by the remote second computing device includes live video and sending the information requested by the remote second computing device includes streaming the live video from the camera of the first computing device to the remote second computing device.

3. The computing device of claim 2, wherein determining that the event associated with the responder has occurred includes receiving an input indicative of the event via at least one of the microphone and the camera.

4. The first computing device of claim 3, wherein the input indicative of the event includes an image or images received via the camera.

5. The first computing device of claim 3, wherein the input indicative of the event is received via the microphone, the input indicative of the event is sound indicative of a gunshot, and the event includes the sound being detected.

6. The first computing device of claim 5, wherein the request for information includes a request to enable the camera and sending the information requested by the remote second computing device includes streaming the live video after the first computing device enables the camera of the first computing device in response to the request to enable the camera.

7. The first computing device of claim 5, wherein determining that the event associated with the responder has occurred includes processing the sound to determine whether the sound is indicative of the gunshot.

8. The first computing device of claim 7, wherein the indication of the event and the information requested by the remote second computing device are sent via a same cellular network.

9. The first computing device of claim 7, wherein the request for information includes a request for a status of a holster, obtaining the information requested by the remote second computing device includes obtaining holster status information from a holster sensor in communication with the first computing device, and sending the information requested by the remote second computing device includes sending the holster status information.

10. The first computing device of claim 7, wherein the instructions in response to execution by the processor cause the first computing device to add a dispatch record number to the information requested by the remote second computing device prior to sending the information requested by the remote second computing device.

11. The first computing device of claim 1, wherein the request for information includes a request for data from a responder device in communication with the first computing device.

12. The first computing device of claim 11, wherein the responder device includes a camera positioned on a dashboard of a vehicle, the request for information includes a request for a live video stream from the camera positioned on the dashboard of the vehicle, obtaining the information requested by the remote second computing device includes obtaining the live video stream from the camera positioned on the dashboard of the vehicle, and sending the information requested by the remote second computing device includes sending the live video stream from the camera positioned on the dashboard of the vehicle.

13. The first computing device of claim 11, wherein the responder device includes a biometric sensor, the request for information includes a request for biometric data, obtaining the information requested by the remote second computing device includes obtaining the biometric data from the biometric sensor, and sending the information includes sending the biometric data obtained from the biometric sensor.

14. The first computing device of claim 11, wherein the responder device includes a holster sensor, the request for information includes a request for a status of a holster, obtaining the information requested by the remote second computing device includes obtaining holster status information from the holster sensor, and sending the information requested by the remote second computing device includes sending the holster status information obtained from the holster sensor.

15. The first computing device of claim 1, wherein the request for information includes a request for a live audio stream of sound received by the microphone of the first computing device and sending the information requested by the remote second computing device includes sending the live audio stream of sound received by the microphone of the first computing device.

16. The first computing device of claim 15, wherein determining that the event associated with the responder has occurred includes receiving an input indicative of the event via the microphone, the input indicative of the event is sound indicative of a gunshot, and the event includes the sound being detected.

17. The first computing device of claim 16, wherein determining the event associated with the responder has occurred includes processing the sound to determine whether the sound is indicative of the gunshot.

18. The first computing device of claim 17, wherein the information requested by teh remote second computing device is obtained directly from both the microphone of the first computing device and the camera of the first computing device.

19. A system for aiding communications between a responder and a dispatch unit, the system comprising:
a first computing device of the dispatch unit, the first computing device comprising:
a processor; and
a memory having instructions stored thereon, the instructions in response to execution by the processor cause the first computing device to:
receive an indication of an event associated with the responder via at least one network,
responsive to receiving the indication of the event, send a request for information; and
receive the information; and
a second computing device of the responder, the second computing device comprising:
a microphone;
a camera;
a second processor; and
a second memory having second instructions stored thereon, the second instructions in response to execution by the second processor cause the second computing device to:
determine that the event has occurred;
automatically send the indication of the event to the first computing device in response to determining that the event has occurred;
receive, from the first computing device, the request for the information;
obtain the information; and
send the information to the first computing device, wherein the information is obtained directly from one or more of the microphone of the second computing device and the camera of the second computing device.

20. The system of claim 19, wherein:
determining that the event has occurred includes receiving sound via the microphone, processing the received sound to determine whether the sound is indicative of a gunshot, and determining that the event has occurred when the processed sound is determined to be indicative of the gunshot;
the information includes live video; and
sending the information includes streaming the live video from the camera of the second computing device to the first computing device.

21. The system of claim 19, wherein:
determining that the event has occurred includes receiving sound via the microphone, processing the received sound to determine whether the sound is indicative of a gunshot, and determining that the event has occurred when the processed sound is determined to be indicative of the gunshot;
the information includes a live audio stream of sound received by the microphone of the second computing device; and
sending the information includes sending the live audio stream of sound received by the microphone of the second computing device.

22. The system of claim 19, wherein:
the request for the information includes a request for data from a responder device in communication with the second computing device;
the responder device includes a camera positioned on a dashboard of a vehicle;
the request for the information includes a request for a live video stream from the camera positioned on the dashboard of the vehicle;
obtaining the information includes obtaining the live video stream from the camera positioned on the dashboard of the vehicle; and
sending the information includes sending the live video stream from the camera positioned on the dashboard of the vehicle.

23. The system of claim 19, wherein:
the request for the information includes a request for data from a responder device in communication with the second computing device;

the responder device includes a biometric sensor;

the request for the information includes a request for biometric data;

obtaining the information includes obtaining the biometric data from the biometric sensor; and sending the information includes sending the biometric data obtained from the biometric sensor.

24. The system of claim 19, wherein:

the request for the information includes a request for data from a responder device in communication with the second computing device;

the responder device includes a holster sensor;

the request for information includes a request for a status of a holster;

obtaining the information includes obtaining holster status information from the holster sensor; and sending the information includes sending the holster status information obtained from the holster sensor.

25. The first computing device of claim 3, wherein obtaining the information requested by the second computing device includes immediately accessing the live video.

26. The system of claim 19, wherein the information includes live video already accessible to the second computing device; and obtaining the information includes accessing the live video already accessible to the second computing device.

\* \* \* \* \*